United States Patent [19]

Ozaki et al.

[11] Patent Number: 5,482,847
[45] Date of Patent: Jan. 9, 1996

[54] ESTERASE GENES, ESTERASE, RECOMBINANT PLASMIDS AND TRANSFORMANTS CONTAINING THE RECOMBINANT PLASMID AND METHODS OF PRODUCING OPTICALLY ACTIVE CARBOXYLIC ACIDS AND THEIR ENANTIOMERIC ESTERS USING SAID TRASNFORMANTS

[75] Inventors: Eiji Ozaki; Akihiro Sakimae, both of Otake; Ryozo Numazawa, Nagoya, all of Japan

[73] Assignee: Mitsubishi Rayon Co., Ltd., Japan

[21] Appl. No.: 183,213

[22] Filed: Jan. 14, 1994

Related U.S. Application Data

[62] Division of Ser. No. 882,329, May 13, 1992, Pat. No. 5,308,765.

[30] Foreign Application Priority Data

| May 15, 1991 | [JP] | Japan | 3-110628 |
| May 15, 1991 | [JP] | Japan | 3-110629 |
| Sep. 27, 1991 | [JP] | Japan | 3-249923 |
| Oct. 15, 1991 | [JP] | Japan | 3-266136 |

[51] Int. Cl.$^6$ .............................. C12N 9/16; C07K 14/21
[52] U.S. Cl. ............................................. 435/196; 530/350
[58] Field of Search .................. 435/196, 252.3, 435/136, 873

[56] References Cited

U.S. PATENT DOCUMENTS

| 4,629,701 | 12/1986 | Sakimae et al. | 435/130 |
| 5,273,897 | 12/1993 | Sato et al. | 435/196 |

FOREIGN PATENT DOCUMENTS

| 0130752A2 | 6/1984 | European Pat. Off. . |
| 0233656A1 | 8/1987 | European Pat. Off. . |
| 0268452A3 | 5/1988 | European Pat. Off. . |
| 0268456A3 | 5/1988 | European Pat. Off. . |
| 0414247A2 | 2/1991 | European Pat. Off. . |
| 60-12993 | 1/1985 | Japan . |
| 60-12992 | 1/1985 | Japan . |
| 1067190 | 3/1989 | Japan . |
| 64-67190 | 3/1989 | Japan . |
| 1222798 | 9/1989 | Japan . |
| 1-222798 | 9/1989 | Japan . |

OTHER PUBLICATIONS

Choi et al., 1990, Agric. Biol. Chem. 54(8):2039–2045.
Kamphuis et al., 1987, Proc. 4th Eur. Congr. Biotechnol., 4:331–348.
London et al., 1984, App. Environ. Microbiol., 47(5):993–997.

*Primary Examiner*—Mindy B. Fleisher
*Assistant Examiner*—David Schmickel
*Attorney, Agent, or Firm*—Pennie & Edmonds

[57] ABSTRACT

The present invention relates to a DNA fragment containing a nucleotide sequence that encodes an amino acid sequence of esterase, said esterase asymmetrically hydrolyzing carboxylic acid esters represented by the formula (I);

$$R_1-COS-(CH_2)n-CH(R_2)-COOR_3$$

(wherein $R_1$ is alkyl, aralkyl or aryl, $R_2$ and $R_3$ are alkyl, and n is 1 or 2) an esterase encoded by the DNA fragment, a recombinant plasmid containing the DNA fragment, a microorganism transformed with the recombinant plasmid and methods of producing optically active carboxylic acids and their enantiomeric esters.

1 Claim, 5 Drawing Sheets

ESTERASE GENES, ESTERASE, RECOMBINANT PLASMIDS AND TRANSFORMANTS CONTAINING THE RECOMBINANT PLASMID AND METHODS OF PRODUCING OPTICALLY ACTIVE CARBOXYLIC ACIDS AND THEIR ENANTIOMERIC ESTERS USING SAID TRASNFORMANTS

This application is a division of application Ser. No. 07/882,329 filed May 13, 1992 now U.S. Pat. No. 5,308,765.

BACKGROUND OF THE INVENTION

The present invention relates to a DNA fragment containing a nucleotide sequence encoding esterase which is highly heat stable and asymmetrically hydrolyzes carboxylic acid esters, an esterase encoded by the DNA fragment, a recombinant plasmid containing the DNA fragment, a microorganism transformed with the recombinant plasmid and methods of producing optically active carboxylic acids and their enantiomeric esters.

An optically active carboxylic acid and its enantiomeric ester, which are represented by the general formula (II);

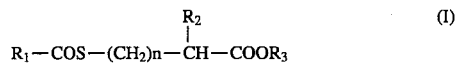

(wherein $R_1$ is alkyl, aralkyl or aryl, $R_2$ is alkyl, and n is 1 or 2), are useful as a raw material of various physiologically active substances.

The present inventors disclosed methods of asymmetrically hydrolyzing a racemic mixture of carboxylic acids esters to produce an optically active carboxylic acid and its enantiomeric ester using an enzyme or a microorganism, the carboxylic acid esters being represented by the general formula (I);

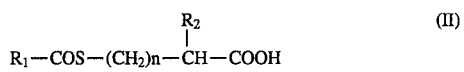

(wherein $R_1$, $R_2$ and n are the same meaning as described above and $R_3$ is alkyl) [see Japanese Patent Application KOKAI No. 12992/1985, No. 12993/1985].

The present inventors isolated *Pseudomonas putida* (FERM BP-3846) from a soil and found that it produces esterase having a potent, asymmetrical hydrolysis activity for a racemic mixture of carboxylic acid esters, and disclosed the bacterium in Japanese Patent Application KOKAI No. 222798/1989).

To obtain a microorganism having an enhanced enzymatic activity, the recombinant DNA technology is often utilized these days. There has been a method known in the art in which a transformed microorganism is used to increase the production of esterase involved in hydrolysis reaction: a DNA fragment encoding an esterase gene derived from *Pseudomonas fluorescens* IFO3018 is prepared; a host microorganism is transformed with a plasmid having the DNA fragment; esterase is produced from the transformed microorganism (Japanese Patent Application KOKAI No. 67190/1989).

Typically, bacterial cells are directly utilized as "enzyme" rather than utilizing an enzyme purified by a complicated manipulation such as isolation and purification when carboxylic acid esters of the formula (I) are required to be asymmetrically hydrolyzed. In such a method, an efficient reaction relies on several factors such as a potent enzyme activity of bacterial cells, the property of an enzyme that serves to produce carboxylic acids with high optical purity and stability in various conditions such as temperature, pH and the like.

Heat labile enzymes are susceptible to thermal inactivation as reaction time progresses so that it is not easy to increase a reaction rate by raising reaction temperature or to reuse recovered enzyme. Bacterial cells that produce enzyme, which has an excellent heat stability and potent enzymatic activity, are necessary for efficient reaction.

The recombinant DNA technology is an effective method of increasing the enzymatic activity of enzyme produced by bacteria as described in Japanese Patent Application KOKAI No. 67190/1989. The properties of enzyme essentially depends on a DNA sequence that encodes an enzyme. To obtain a highly stable enzyme that satisfies the above requirement, one needs to find a DNA fragment encoding the enzyme.

The Japanese Patent Application KOKAI No. 67190/1989 discloses a microorganism transformed with a recombinant plasmid containing a DNA fragment. The DNA fragment comprises the sequence encoding an esterase gene derived from *Pseudomonas fluorescens* IFO3018. Esterase produced by the microorganism is less heat stable and is inactivated in several hours, for example, at 45° C. or more.

It is a primary object of the present invention to prepare a DNA fragment encoding a highly heat stable esterase for the asymmetrically hydrolysis of carboxylic acid esters of the formula (I) and to efficiently carry out the asymmetrical hydrolysis using a transformant that contains the DNA fragment and efficiently produces the enzyme.

The present inventors have investigated an efficient method of asymmetrically hydrolyzing carboxylic acid esters of the formula (I) using enzyme. We have successfully found that a microorganism transformed with a recombinant plasmid containing an esterase gene derived from *Pseudomonas putida* (FERM BP-3846), which is isolated from a soil, is useful for obtaining a high yield of reaction products and for carrying out an efficient reaction in a short period of time. The microorganism produces enzyme having potent enzymatic activity and the enzyme is not inactivated with time even at a reaction temperature of 50° C. or more.

In addition, we have isolated a highly heat stable, novel esterase substantially in a pure form from the transformed microorganism and successfully characterized the physical and chemical properties of the enzyme.

SUMMARY OF THE INVENTION

The present invention provides a DNA fragment containing a nucleotide sequence that encodes the amino acid sequence of esterase as described in SEQ ID No. 2, said esterase asymmetrically hydrolyzing carboxylic acid esters represented by the formula (I);

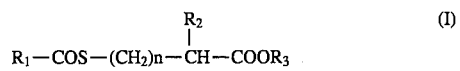

(wherein $R_1$ is alkyl, aralkyl or aryl, $R_2$, $R_3$ are alkyl, and n is 1 or 2) to give an optically active carboxylic acid represented by the formula (II);

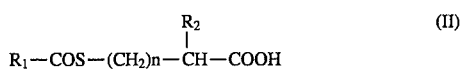

(wherein $R_1$, $R_2$, and n are the same meaning as described above).

In addition, the present invention provides an esterase having an amino acid sequence as described in SEQ ID No. 2, an esterase encoded by a DNA fragment as described in SEQ ID No. 3, a recombinant plasmid containing the DNA fragment and a microorganism transformed with the recombinant plasmid.

Furthermore, the present invention provides a method of producing optically active carboxylic acids represented by the formula (II) and their enantiomeric esters, by reacting a racemic mixture of carboxylic acid esters represented by the formula (I) with the culture or bacterial cells of the transformant or bacterial-cell-treated materials.

The method of the present invention efficiently produce optically active carboxylic acids represented by the formula (II), and their enantiomeric esters from a racemic mixture of carboxylic acid esters represented by the formula (I).

The esterase of the present invention has the following physical and chemical properties.

(1) Optimum pH: 7.0 (see FIG. 4)
(2) Stability of esterase in varied pH: 6.0–8.0 (see FIG. 5)
(3) Optimum temperature: 60°–70° C. (see FIG. 6)
(4) Heat stability: up to 70° C. (see FIG. 7)
(5) Molecular weight: about 30,000 (by SDS-PAGE)
(6) Isoelectric point: pH 3.90±0.1 (by isoelectric focusing)
(7) Amino acid sequence: sequence described in SEQ ID No. 2
(8) Specificity: mainly hydrolyze carboxylic acid esters having 8 or less carbon atoms as well as aromatic alcohols such as acetyl esters

Figure 1:
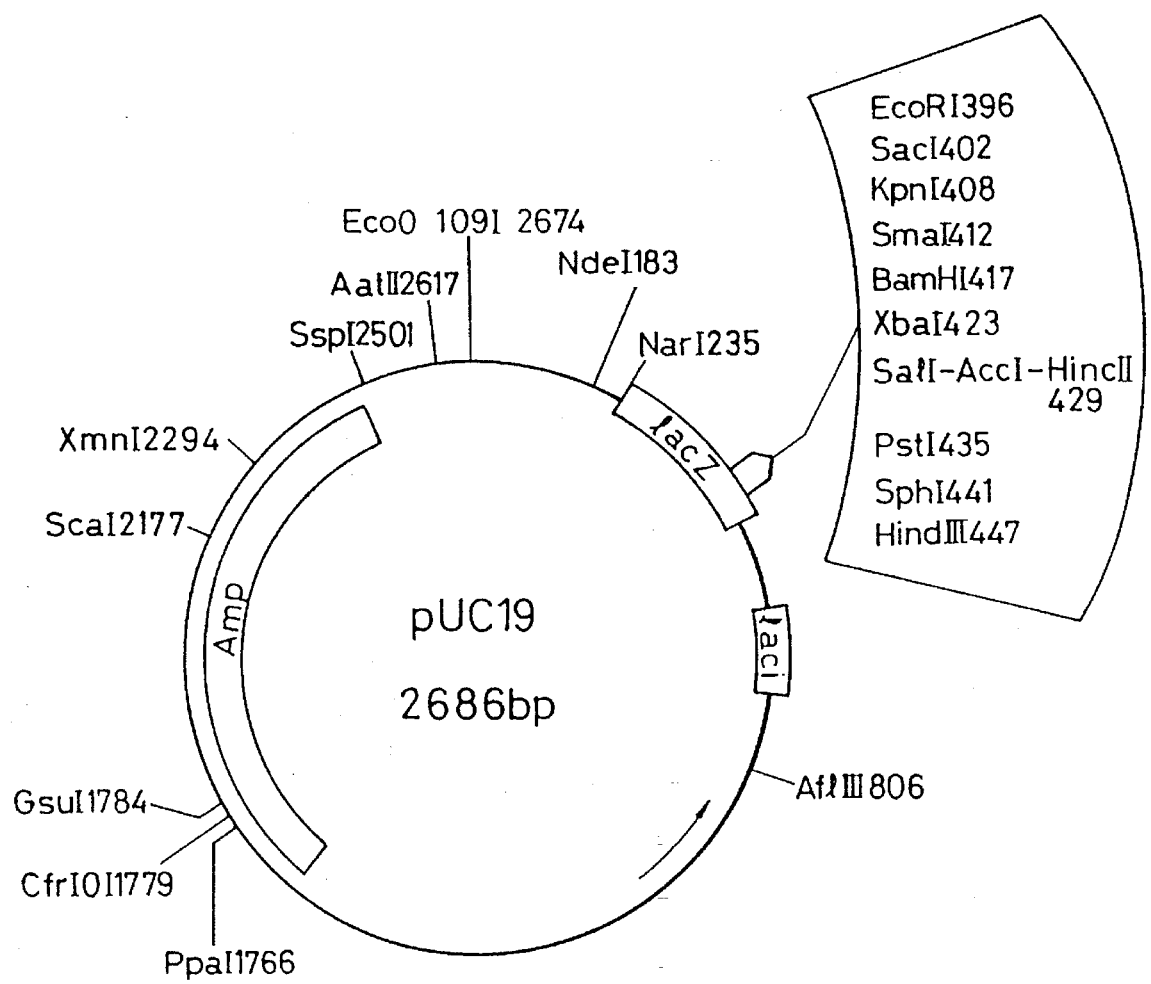
FIG. 1 shows the cloning vector pUC19.

In the Figures, the symbols are defined as follows:
Amp=ampicillin resistance coding region
lacZ=β-galactosidase structural gene
lac i=repressor structural gene
1=region derived from pUC19
2=region derived from the chromosomal DNA of *Pseudomonas putida*
B=BglII
C=ClaI
EI=EcoRI
EV=EcoRV
P=PvuII
S=SalI
Sm=SmaI
Ps=PstI

DETAILED DESCRIPTION OF THE INVENTION

In the general formula (I) and (II), preferable alkyl represented by $R_1$ is ($C_1$–$C_6$) alkyl, for example, methyl and ethyl, aralkyl is, for example, benzyl, aryl is, for example, phenyl, and preferable alkyl represented by $R_2$ or $R_3$ is ($C_1$–$C_6$) alkyl, for example, methyl and ethyl.

Carboxylic acid esters represented by the formula (I), include methyl β-acetylthio-α-methylpropionate, methyl S-acetyl-β-mercaptoisobutyrate, methyl S-acetyl-γ-mercapto-α-methyl-n-butyrate, methyl S-benzoyl-β-mercaptoisobutyrate and methyl S-phenylacetyl-βmercaptoisobutyrate.

The DNA fragment of the present invention includes, for example, a DNA fragment comprising the whole or part of a nucleotide sequence described in SEQ ID No. 1 and a DNA fragment comprising the whole or part of a nucleotide sequence described in SEQ ID No. 3.

In addition, the DNA fragment of the present invention may be obtained by cloning a desirable esterase gene derived from the chromosome of a microorganism or by synthesizing a desirable sequence by a DNA synthesizer.

The nucleotide sequence may be a single-stranded or a double-stranded DNA. Either of them can be used in the present invention.

Microorganisms suitable as a chromosome donor in cloning are, for example, *Pseudomonas putida* (FERM BP-3846).

The following will illustrate cloning of a DNA fragment containing a whole nucleotide sequence described in SEQ ID No. 1.

Chromosomal DNA is obtained from *Pseudomonas putida* (FERM BP-3846) by the Marmur et al method [J.Marmur et al., J.Mol.Biol., 3:208, 1961] and is then partially digested with EcoRI. After digestion, restriction fragments are obtained.

The plasmid pUC19 was digested with EcoRI, which cleaves the EcoRI site of a multiple cloning site in the lacZ gene(one of the genes in lac operon of *E. coli*) to give a linear DNA.

The EcoRI digested chromosomal DNA and pUC19 are ligated using T4 DNA ligase.

The reaction product is used to transform $CaCl_2$-treated *E. coli* JM105 cells (one of the strains of *E. coli* K-12). The transformation mixture is spread on an LB agar plate containing ampicillin, IPTG (isopropyl β-D-thiogalactopyranoside) and X-Gal (5-bromo-4-chloro-3-indolyl-β-D-galactopyranoside), and incubated.

Transformants containing the DNA-fragment-free pUC19 at its EcoRI site become ampicillin resistance and grow to form colonies. When induced by IPTG, these transformants also express β-galactosidase that cut X-Gal to make blue colonies. Conversely, transformants containing the DNA-fragment-containing pUC19 at its EcoRI site become ampicillin resistance and are unable to express β-galactosidase. These transformants make white colonies.

After incubation on a plate, positive transformants are selected by picking white colonies. The positive transformants are then screened for esterase activities.

Screening may be carried out as described below. The colonies on the plate are transferred to a filter paper soaked in a solution of 10 mM Tris-HCl/pH 7.5, 0.01% bromocresolpurple and 100 ppm of methyl DL-β-acetylthio-α-methylpropionate. The filter is incubated at room temperature for several hours. Transformants having an esterase activity produce carboxylic acid and change the color of bromocresolpurple (pH indicator) from purple to yellow around the colony because of a decrease of pH. Transformants having an esterase gene can be, therefore, observed with the naked eye.

The position of an esterase gene in the recombinant plasmid is determined by the following method.

Plasmids are isolated from the transformant having an esterase activity. EcoRI DNA fragments are then obtained by digesting the plasmid DNA with EcoRI. The EcoRI digest is further digested with various restriction enzymes. The restriction fragments are inserted into the plasmid pUC19 to give recombinant plasmids. E. coli JM105 is transformed with the recombinant plasmids. The transformants are tested for an esterase activity. Among the positive transformants, a transformant comprising a minimum length DNA fragment for an esterase gene expression is selected. The nucleotide sequence of the DNA fragment is determined by various methods and SEQ ID No. 1 is obtained.

Cloning vectors include the pBR and pUC series that are a high-copy-number plasmid stably maintained in E. coli, pHY300PLK used for Bacillus subtilis and vectors derived from RSF1010 that have a wide host range.

Host microorganisms used for transformation include E. coli, yeast, Bacillus subtilis and Actinomycetes.

Microorganisms transformed with a recombinant plasmid containing a esterase gene encoding a heat stable esterase produce enzyme that has similar enzymatic properties to those of a parental strain, Pseudomonas putida (FERM BP-3846). In addition, the transformant has by far higher enzymatic activity than the DNA donor bacterium because the transformant contains a high-copy-number plasmid. The transformant is grown in a culture medium and used in a form such as culture, bacterial cells or bacterial-cell-treated materials.

The transformed microorganism is typically grown in a liquid culture medium or in a solid culture medium. For example, an LB culture medium can be used. Culture is carried out at 10°–50° C., pH 2–11. Aeration agitation culture is also utilized to facilitate growth. Hydrolysis may be carried out by adding carboxylic acid esters of the formula (I) to culture at the beginning of culture or in the middle of culture or after completion of culture.

Alternatively, grown bacterial cells are harvested by centrifugation and may be added to a solution containing carboxylic acid esters of the formula (I). When bacterial cells are used, bacterial cells are dried by, for example, lyophilization or spray-drying, or are treated by organic solvents such as acetone or toluene, or are disrupted to give broken cells, or are extracted to give bacterial-cell-treated materials. Solvents used for reaction include deionized water or buffer. The preferable concentration of carboxylic acid esters of formula (I) in a solvent or in a culture medium may be 0.01–50 wt %. Carboxylic acid esters of formula (I) suspended in water may be added to carry out reaction. Solvents, methanol or acetone, may be added to help dissolve esters. The pH of a reaction mixture is 2–11, preferably 5–8. As reaction proceeds, the pH of a reaction mixture decreases due to the increase of the reaction product, optically active carboxylic acids of the formula (II). The pH of a reaction mixture should be adjusted with an appropriate neutralizing agent. An enzyme produced by the transformant of the present invention is highly heat stable so that reaction temperature may be in the range of 5°–80° C. If the property of the enzyme produced by the transformant of the present invention is attempted to be optimized, 45° C. or more is preferable for reaction. At that temperature range, the enzyme can maintain its activity during reaction.

Isolation and purification of a reaction product from a reaction mixture or a culture may be carried out by the method known in the art, for example, extraction, recrystalization and column chromatography.

A novel esterase, one of the present invention, may be obtained from the culture of the transformant of tile present invention by tile method known in the art: Enzyme endogenously produced in the transformant is extracted by any method in the art to give bacterial-cell free extract. The extract is concentrated using ammonium sulfate, loaded on an ion-exchange chromatography column, gel-filtrated or is repetitiously subjected to the procedure described above to give pure enzyme.

EXAMPLE

Example 1

1-(1) Preparation of Chromosomal DNA

Chromosomal DNA was isolated from Pseudomonas putida (FERM BP-3846) by the Marmur et al method [J,Marmur et al., J.Mol.Biol., 3:208, 1961] as described below:

Pseudomonas putida (FERM BP-3846) was inoculated into 100 ml of an LB culture medium (1% polypeptone, 0.5% yeast extract, 0.5% NaCl) and incubated at 37° C. overnight. After the incubation, bacterial cells were harvested by centrifugation and about 3 g of bacterial cells (wet weight) was then suspended in 24 ml of TEG buffer [25 mM Tris-HCl, 10 mM EDTA (ethylenediaminetetraacetic acid), 50 mM glucose, pH8.0 ]. 1 ml of lysozyme (suspended in TEG buffer, concentration: 10 mg/ml) was added to the suspension. The suspension was stirred at 32° C. for 30 minutes. After the stirring, 2 ml of a 12.5% SDS solution was added to the bacterial lysate. The mixture was stirred. 6.75 ml of a 5M sodium perchlorate solution was added to the lysate mixture. The lysate mixture was stirred. 33.8 ml of a chloroform/isoamylalcohol [24:1(v/v)] mixture was added to the lysate mixture. The mixture was gently stirred for 30 minutes.

After the stirring, the mixture was centrifuged. The supernatant was saved. Two volume of ice cold ethanol was gently added to the supernatant. DNA was removed from ethanol by winding it with a glass stick. The DNA was dissolved in 9 ml of 0.1×SSC (15 mM NaCl, 1.5 mM sodium citrate). 1 ml of 10×SSC (1.5M NaCl, 150 mM sodium citrate) was added to the DNA solution. RNaseA was added to the DNA solution to a final concentration of 50 μg/ml. The DNA mixture was gently stirred for 30 minutes. After the stirring, 10.2 ml of a chloroform/isoamylalcohol [24:1(v/v)]mixture was added to the DNA mixture. The mixture was gently stirred for 30 minutes.

After the stirring, the mixture was centrifuged. The supernatant was saved. 1 ml of an acetic acid/EDTA (3M sodium acetate, 0.01M EDTA, pH 7.0) mixture was added to the supernatant. Isopropylalcohol (total volume: 5.4 ml) was dropwise added to the mixture while stirring the mixture with a glass stick. DNA was removed by winding it with a glass stick. The DNA was dissolved in 3 ml of 1×SSC (0.15M NaCl, 15 mM sodium citrate) to give 2 µg/µl of DNA.

1-(2) Preparation of Recombinant Plasmids

EcoRI was added to 5 µl of chromosomal DNA (corresponds to 10 µg of DNA) obtained in 1-(1) to a final concentration of 2 units/µg DNA. The reaction mixture was incubated at 37° C. for 30 minutes according to the method known in the art. After the incubation, EcoRI partially digested DNA was obtained. In the meantime, 1 µg of plasmid pUC19 DNA was digested with EcoRI according to the method known in the art to give a linear plasmid DNA.

The digested chromosome DNA fragments and pUC19 fragments were combined. T4 DNA ligase was added to the DNA mixture and incubated to give a ligation product.

1-(3) Isolation of Recombinant Plasmids

E. coli JM105 (TAKARA SYUZO Co., LTD) was grown in an LB culture medium at 37° C. for 2–3 hours. After the incubation, bacterial cells were harvested by centrifugation. The bacterial cells were suspended in an ice cold 50 mM $CaCl_2$ solution. The suspension was then centrifuged. The cell pellet was resuspended in a fresh 50 mM $CaCl_2$ solution. The suspension was placed on ice for 30 minutes.

After 30 minute incubation, about 100–200 µl of the suspension was transferred to an Eppendorf tube. The ligation product (about 2 µg of DNA) obtained in 1-(2) was added to the tube. The tube was further incubated on ice for 30 minutes. The bacterial cells were then heat-shocked at 42° C. for 2 minutes. 1 ml of an LB culture medium was added to the tube, which was incubated at 37° C. for 60 minutes.

After the incubation, the transformation product, about 100 µl each, was spread on an LB agar culture medium plate containing 100 µg/ml of ampicillin, 0.5 mM IPTG, 0.2% X-Gal. The plate was incubated at 37° C. overnight.

Of colonies appeared on the plate, white colonies were tested for esterase activity. Positive transformants that contain recombinant plasmids comprising an esterase gene were selected as described below.

Measurement of Esterase Activity

The white colonies on the plate were transferred to a filter paper soaked in a solution of 10 mM Tris-HCl/pH 7.5, 0.01% bromocresolpurple and 100 ppm of methyl DL-β-acetylthio-α-methylpropionate. The filter was incubated at room temperature for several hours. Transformants having a esterase activity produced carboxylic acid, which changed the color of bromocresolpurple (pH indicator) from purple to yellow around the colony because of a decrease of pH. Positive transformants that contain recombinant plasmids comprising an esterase gene were thus obtained.

Figure 2:
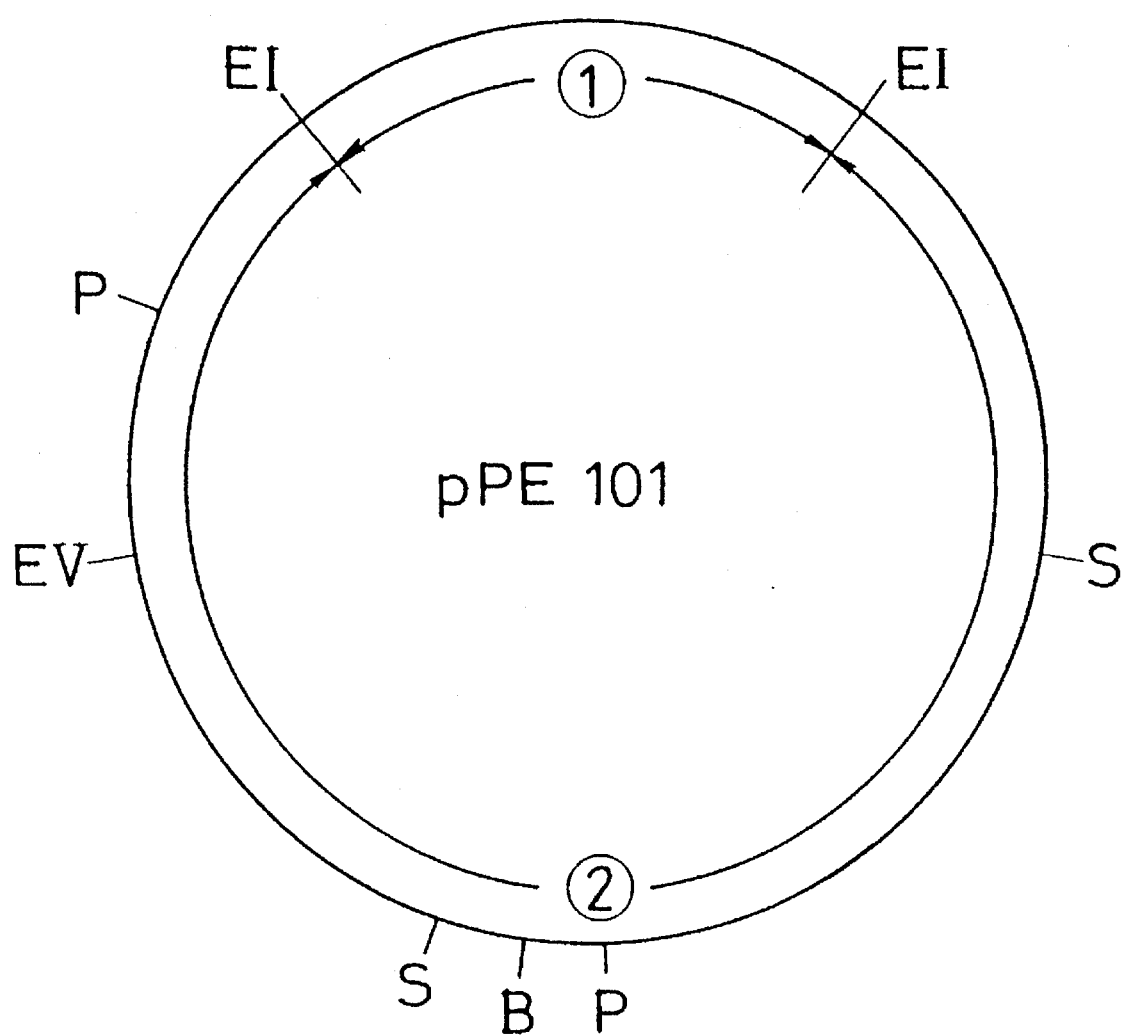
FIG. 2 shows a restriction map of recombinant plasmid pPE101 comprising the DNA fragment that contains the esterase structural gene of the present invention.

One of the positive transformants was grown and the plasmid DNA was prepared according to the method described by Birnboim et al., in Nucleic acid Res., 7: 1513–1523, 1979. The restriction map of the plasmid was constructed and is shown in FIG. 2. The recombinant plasmid shown in FIG. 2 was designated as pPE101.

1-(4) Esterase Gene Region in pPE101 pPE101 was digested with EcoRI according to the method known in the art. The restriction fragments were electrophoresed and a DNA fragment having EcoRI ends (large EcoRI digest) was obtained. The large EcoRI digest was further digested with various restriction enzymes to give smaller DNA fragments. Several restriction maps are shown in FIG. 3.

The smaller DNA fragments were then inserted into a multiple cloning site within the lac Z region of pUC19. The resulting recombinant plasmids were used to transform E. coli JM105. Transformants were tested for esterase activity.

Preparation of plasmid DNA, transformation and measurement of esterase activity were carried out according to the methods described in 1-(2) and (3). When inserting the smaller fragments into the pUC19, a linker was synthesized and used if it was necessary.

Figure 3:
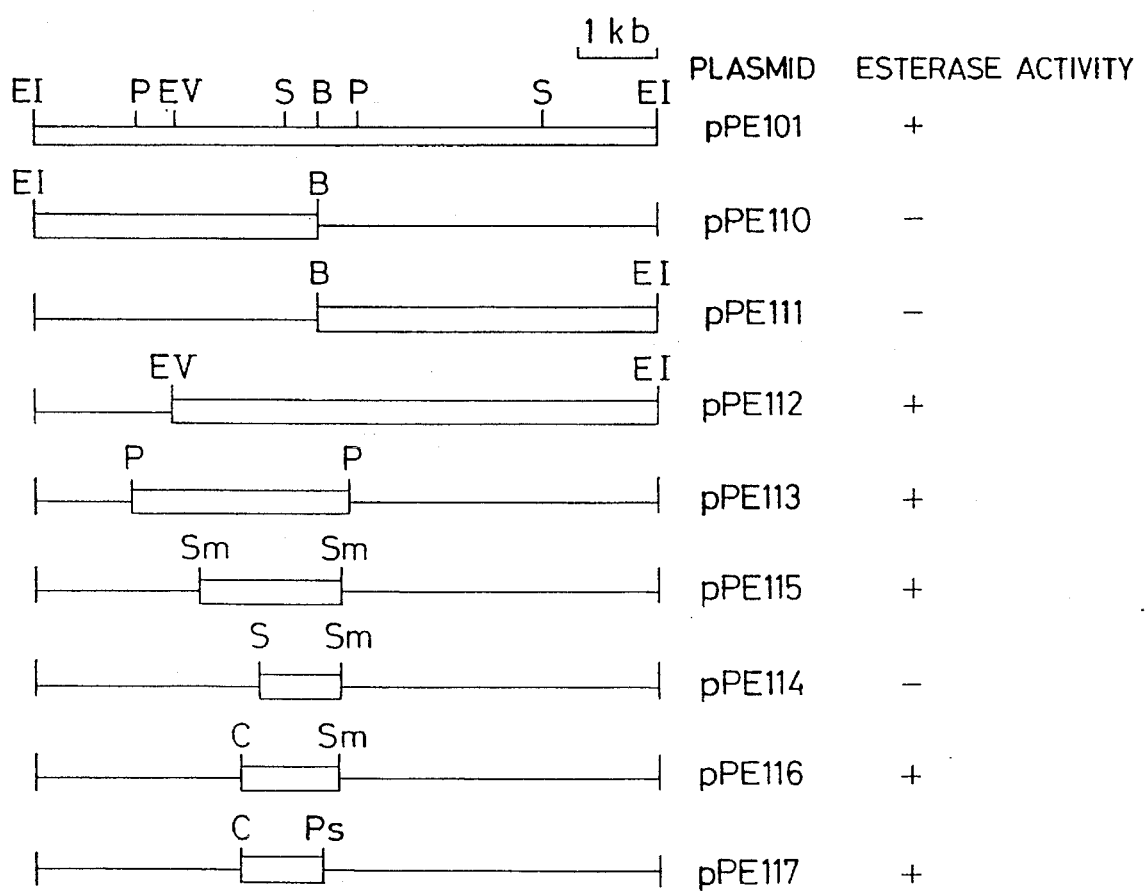
FIG. 3 shows deleted DNA fragments and their positions relative to the EcoRI fragment in pPE101, a recombinant plasmid constructed by incorporating the DNA fragment into the pUC19, and esterase activity of microorganisms transformed with the recombinant plasmids.

The esterase activity of the transformant is also shown in FIG. 3. According to the esterase activity, about 1.3 kb ClaI/SmaI DNA fragment and about 1.2 kb ClaI/PstI DNA fragment were found to contain an esterase gene.

E. coli JM105 transformed with the plasmid pPE116 was designated as E. coli JM105 (pPE116). E. coli JM105 (pPE116) was deposited with Fermentation Research Institute, Agency of Industrial Science and Technology, under the name of MR-2101, and assigned the accession number FERM BP-3838.

E. coli C600 transformed with the plasmid pPE117 was designated as E. coli C600 (pPE117). E. coli C600 (pPE117) was deposited with Fermentation Research Institute, Agency of Industrial Science and Technology, under the name of MR-2103, and assigned the accession number FERM BP-3835.

1-(5) Nucleotide Sequence of Esterase Structural Gene

The whole nucleotide sequence of the ClaI/SmaI DNA fragment obtained in 1-(4) was determined by the dideoxy chain termination method (F. Sanger, Science., 214:1205, 1981) using a phage vector. The nucleotide sequence was then analyzed and the positions of an SD sequence and a DNA sequence essential for an enzyme activity were located. Based on the analysis, an open reading frame and a corresponding amino acid sequence were determined. The results are shown in SEQ ID No. 4.

1-(6) Nucleotide Sequences of Esterase Gene and Deduced Amino Acid Sequences

The whole nucleotide sequence of the DNA fragment in pPE117 was determined by the dideoxy chain termination method (F. Sanger, Science., 214:1205, 1981) using M13 phage vector. The nucleotide sequence of about 1.2 kb DNA fragment derived from the chromosomal DNA of Pseudomonas putida (FERM BP-3846) is the one described in SEQ ID No. 3. The study of the nucleotide sequence described in SEQ ID No. 3 revealed the following: only an open reading frame encompassing the region essential for enzyme activity is present in the nucleotide sequence described in SEQ ID No. 1; an SD sequence situated several bases upstream of the translation initiation codon as well as the open reading frame is present in the nucleotide sequence described in SEQ ID No. 3. The amino acid sequence deduced from the nucleotide sequence described in SEQ ID No. 1 is shown in SEQ ID No. 2.

1-(7) Asymmetrical Hydrolysis of Methyl DL-β-acethylthio-α-methylpropionate

E. coli JM105 (pPE116) was cultured with shaking in 500 ml of an LB culture medium containing 50 µg/µl of ampicillin at 37° C. overnight. After incubation, bacterial cells were harvested by centrifugation. The whole bacterial cell was suspended in 200 ml of a 5% methyl DL-β-acetylthio-α-methylpropionate solution. The reaction was carried out at 45° C. for three hours while adjusting the pH with 0.1N NaOH to pH 7. After the reaction, the bacterial cells were removed by centrifugation. Unreacted methyl β-acetylthio-α-methylpropionate in the supernatant was removed using ethyl acetate. The pH of the aqueous layer of the resultant extract was adjusted with diluted sulfuric acid to 2.0 or less. The mixture was then extracted with ethyl acetate to give a D-β-acetylthio-α-methylpropionate extract. Anhydrous sodium sulfate was added to the extract. After dehydration, the solvent was vapored out to give oily substance. Part of the substance was removed and diluted with water. The resulting diluted sample was subjected to a quantitative analysis of β-acetylthio-α-methylpropionate by HPLC. Additionally, part of the substance was dissolved in chloroform. The optical rotation of the resulting sample was polarimetrically analyzed (PM-101, Union Giken). As a result, 1.5 g of a desired product was obtained. Specific rotation was calculated by the following equation:

$$[\alpha]^{25} = -58.1 \ (C=2.00 \ CHCl_3)$$

The specific rotation was −58.3, which was the same value as that of a sample obtained from *Pseudomonas putida* (FERM BP-3846).

1-(8) Measurement of Esterase Activity

*E. coli* C600 (pPE117) cells were tested for asymmetric hydrolysis of methyl DL-β-acetylthio-α-methylpropionate according to the similar method described in 1-(7).

The enzymatic activity of *Pseudomonas putida* (FERM BP3846), *E. coli* JM105 (pPE116) and *E. coli* C600 (pPE117) during the first one hour was measured and compared. The results are shown in Table 1.

TABLE 1

| Bacterial strain | Relative specific activity* |
| --- | --- |
| *Pseudomonas putida* (FERM BP-3846) | 1 |
| *E. coli* JM105 (pPE116)[FERM BP-3838] | 2 |
| *E. coli* C600 (pPE117)[FERM BP-3835] | 200 |

*Pseudomonas putida (FERM BP-3846) is assumed to be 1

As is shown in Table 1, the specific activity of *E. coli* C600 (pPE117) [FERM BP-3835] is about 200 times as much as that of *Pseudomonas putida* (FERM BP-3846).

Example 2

Heat Stability Test of Esterase

*Pseudomonas fluorescens* IFO3018, *Pseudomonas putida* 2068 (FERM BP-3846) and *E. coli* JM105 (pPE116) [FERM BP-3838] were separately grown in the following condition.

(a) *Pseudomonas fluorescens* IFO3018:

Culture medium; LB culture medium (500 ml)

Growth temperature; 30° C.

Incubation period; overnight (b) *Pseudomonas putida* 2068 (FERM BP-3846):

Culture medium; LB culture medium (500 ml)

Growth temperature; 30° C.

Incubation period; overnight (c) *E. coli* JM105 (pPE116) [FERM BP-3838]

Culture medium; LB culture medium containing 50 µg/ml of ampicillin (500 ml)

Growth temperature; 30° C.

Incubation period; overnight

Bacterial cells thus obtained were tested for heat stability of esterase by the method described below.

Bacterial cells were harvested. 1.0 g of the cells (wet weight) was suspended in 100 ml of 0.05M phosphate buffer/pH 7.0 containing 5.0 g of methyl DL-β-acetylthio-α-methylpropionate. The suspension was incubated at 30° C. for enzyme reaction. As the reaction proceeded, 0.1N NaOH was dropwise added to the suspension to maintain the pH at 7.0. The total volume ($Q_1$) of NaOH used to maintain the pH during first one hour was measured.

1.0 g of the cells (wet weight) was suspended in 100 ml of 0.05M phosphate buffer/pH 7.0. The suspension was incubated for three hours at a temperature selected from the range of 20°–80° C. After incubation, 5.0 g of methyl DL-β-acethylthio-α-methylpropionate was added to the suspension. The suspension was incubated at 30° C. for enzyme reaction. As the reaction proceeded, 0.1N NaOH was added dropwise to the suspension to maintain the pH at 7.0. The total volume ($Q_2$) of NaOH used to maintain the pH during first one hour was measured.

Heat unaffected esterase activity is calculated by the following equation;

$$\text{Heat unaffected esterase activity} = (Q_2 \div Q_1) \times 100$$

The results are shown in Table 2.

TABLE 2

| Incubation temperature | Esterase activity Bacterial strain | | |
| --- | --- | --- | --- |
| (°C.) | a | b | c |
| 30 | 100 | 100 | 100 |
| 40 | 85 | 100 | 100 |
| 50 | 70 | 100 | 100 |
| 60 | 30 | 100 | 100 |
| 70 | 5 | 65 | 67 |
| 80 | 0 | 0 | 0 |

As is evident from Table 2, the heat stability of the esterase produced by *Pseudomonas putida* 2068 (FERM BP-3846) and *E. coli* JM105(pPE116) is higher than that of esterase produced by *Pseudomonas fluorescens* IFO3018.

Example 3

3-(1) Purification of Novel Esterase

*E. coli* C600 (pPE117)[FERM BP-3835]was grown in a culture medium (1% polypeptone, 0.5% yeast extract, 0.5% NaCl, 2% glucose, pH 7.0) in aeration-agitation fermenter at 37° C. for 14 hours. Bacterial cells were harvested by centrifugation and 15 g of bacterial cells was obtained. The bacterial cells were suspended in an equal amount of M/20 phosphate buffer. The bacterial cells were sonicated and then centrifuged. The supernatant was saved and concentrated using ammonium sulfate. The concentrate was then put on a DEAE Sephadex D-50 (Pharmacia) column equilibrated with M/20 phosphate buffer. A linear gradient solution, 0–0.5M NaCl, was added to the column to elute esterase. Esterase active fractions were collected and concentrated. The concentrated sample was put on a Sephadex G-100 (Pharmacia) column equilibrated with M/20 phosphate buffer. Esterase was eluted with M/20 phosphate buffer. Esterase active fractions were pooled and concentrated. 500 mg of purified esterase was obtained.

Figure 4:
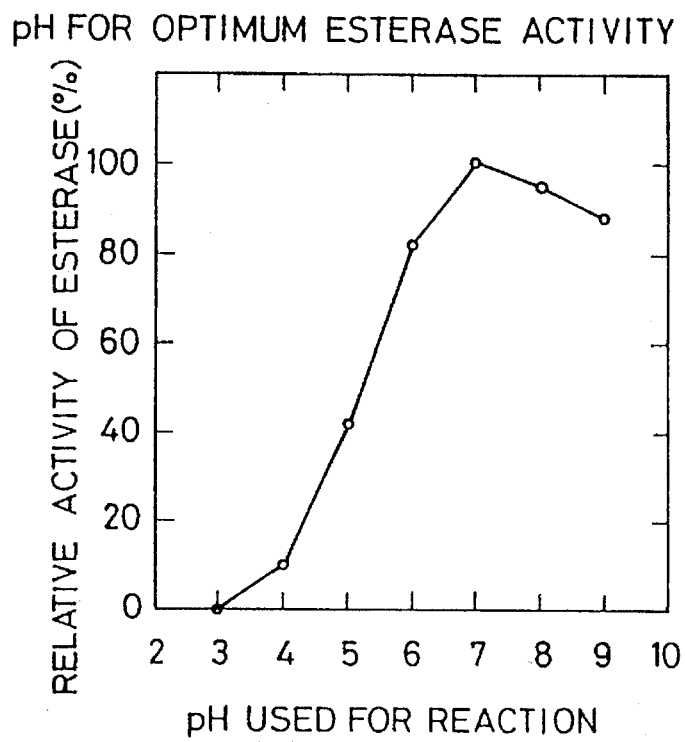
FIG. 4 shows an optimum pH of the esterase of the present invention.
Figure 5:
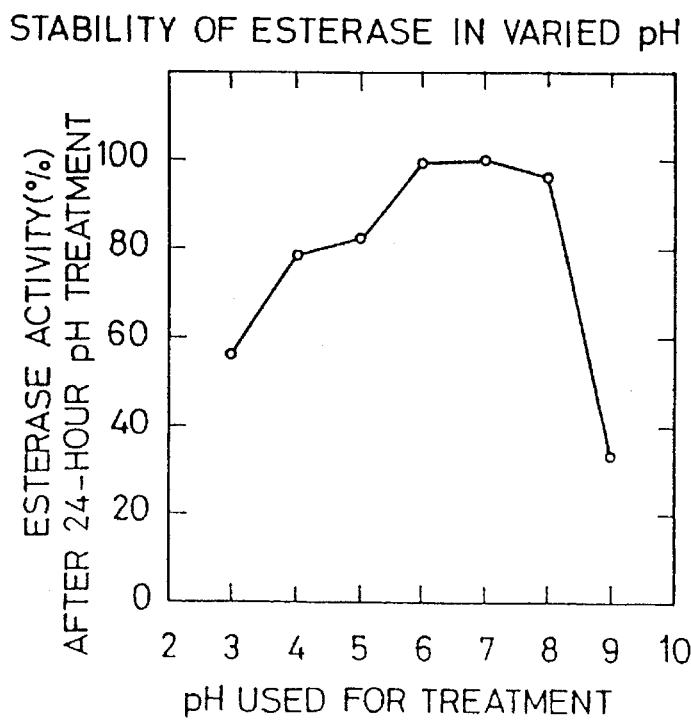
FIG. 5 shows stability of esterase in varied pH.

The molecular weight of the esterase was determined by SDS-PAGE and found that it was about 30,000. The isoelectric point of the esterase was determined by the isoelectric focusing (Fast System, Pharmacia) and found that it was pH 3.90±0.1.

pH for optimum esterase activity and stability of the esterase in different pHs are shown in FIGS. 4 and 5.

Figure 6:
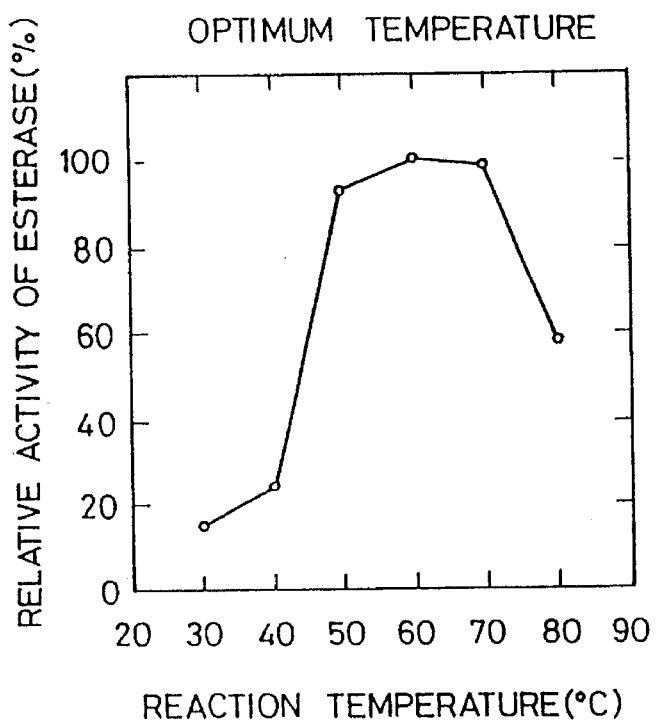
FIG. 6 shows an optimum temperature of the esterase of the present invention.
Figure 7:
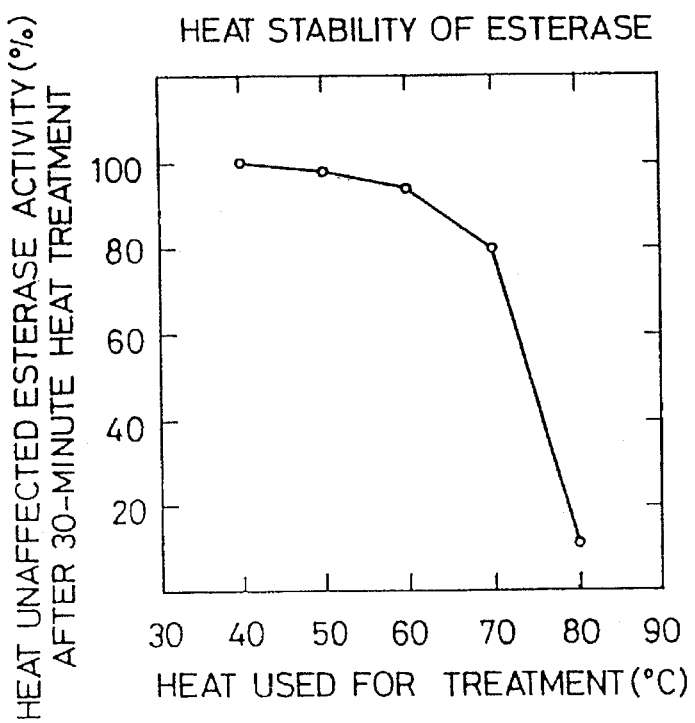
FIG. 7 shows heat stability of the esterase of the present invention.

Temperature for optimum esterase activity and heat stability of the esterase are shown in FIGS. 6 and 7.

3-(2) Analysis of N-terminal Amino Acid Sequence of Novel Esterase

N-terminal amino acid sequence of the novel esterase was analyzed by amino acid sequence autoanalyzer (SHIMADZU CORPORATION) and found as follows:

|   | NH₂ terminus |   |   |   |   |   |   |   | NH₂ terminus |   |   |   |   |   |
|---|---|---|---|---|---|---|---|---|---|---|---|---|---|---|
| 1- | 2- | 3- | 4- | 5- | 6- | 7- | | 5 | Ser | Tyr | Val | Thr | Thr | Lys | Asp |

What is claimed is:

1. An isolated and purified esterase comprising the amino acid sequence described in SEQ ID No. 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 831 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pseudomonas putida
        ( B ) STRAIN: MR-2068 (FERM BP- 3846)

( i x ) FEATURE:
        ( A ) NAME/KEY: 1-831 CDS ( x i ) SEQUENCE DESCRIPTION: SEQ ID NO:1:

| ATGAGCTATG | TAACCACGAA | GGACGGCGTA | CAGATCTTCT | ACAAGGACTG | GGGCCCGCGC | 60 |
| GATGCGCCGG | TCATCCACTT | CCACCACGGC | TGGCCGCTCA | GTGCCGACGA | CTGGGACGCG | 120 |
| CAGATGCTGT | TCTTCCTCGC | CCACGGTTAC | CGCGTGGTCG | CCCACGACCG | CCGCGGCCAT | 180 |
| GGCCGCTCCA | GCCAGGTATG | GGACGGCCAC | GACATGGACC | ACTACGCCGA | CGACGTAGCC | 240 |
| GCAGTGGTGG | CCCACCTGGG | CATTCAGGGC | GCCGTGCATG | TCGGCCACTC | GACCGGTGGC | 300 |
| GGTGAGGTGG | TGCGCTACAT | GGCCCGACAC | CCTGCAGACA | AGGTGGCCAA | GGCCGTGCTG | 360 |
| ATCGCCGCCG | TACCGCCGTT | GATGGTGCAG | ACTCCCGATA | ATCCCGGTGG | CCTGCCCAAA | 420 |
| TCCGTTTTCG | ACGGCTTCCA | GGCCCAGGTC | GCCAGCAACC | GCGCGCAGTT | CTACCGGGAT | 480 |
| GTGCCGGCAG | GGCCGTTCTA | CGGCTACAAC | CGCCCCGGTG | TCGACGCCAG | CGAAGGCATC | 540 |
| ATCGGCAACT | GGTGGCGCCA | GGGCATGATC | GGTAGCGCCA | AGGCCCATTA | CGATGGCATC | 600 |
| GTGGCGTTTT | CCCAGACCGA | CTTCACCGAA | GACCTGAAGG | GCATTACCCA | GCCGGTGCTG | 660 |
| GTGATGCATG | GCGACGACGA | CCAGATCGTG | CCGTATGAGA | ACTCCGGGCT | GCTGTCGGCC | 720 |
| AAGCTGCTGC | CCAATGGCAC | ACTGAAGACC | TACCAGGGCT | ACCCGCATGG | CATGCCGACC | 780 |
| ACCCATGCCG | ATGTGATCAA | TGCGGATTTG | CTGGCGTTTA | TCCGTAGCTG | A | 831 |

( 2 ) INFORMATION FOR SEQ ID NO:2:

( i ) SEQUENCE CHARACTERISTICS:
        ( A ) LENGTH: 276 amino acids
        ( B ) TYPE: amino acid
        ( C ) STRANDEDNESS: single
        ( D ) TOPOLOGY: unknown ( i i ) MOLECULE TYPE: peptide ( v i ) ORIGINAL SOURCE:
        ( A ) ORGANISM: Pseudomonas putida
        ( B ) STRAIN: MR-2068 (FERM BP- 3846)

( x i ) SEQUENCE DESCRIPTION: SEQ ID NO:2:

```
Met  Ser  Tyr  Val  Thr  Thr  Lys  Asp  Gly  Val  Gln  Ile  Phe  Tyr  Lys  Asp
1              5                        10                       15

Trp  Gly  Pro  Arg  Asp  Ala  Pro  Val  Ile  His  Phe  His  His  Gly  Trp  Pro
               20                  25                      30

Leu  Ser  Ala  Asp  Asp  Trp  Asp  Ala  Gln  Met  Leu  Phe  Phe  Leu  Ala  His
          35                       40                 45

Gly  Tyr  Arg  Val  Val  Ala  His  Asp  Arg  Arg  Gly  His  Gly  Arg  Ser  Ser
     50                       55                      60

Gln  Val  Trp  Asp  Gly  His  Asp  Met  Asp  His  Tyr  Ala  Asp  Asp  Val  Ala
65                       70                  75                           80

Ala  Val  Val  Ala  His  Leu  Gly  Ile  Gln  Gly  Ala  Val  His  Val  Gly  His
               85                       90                           95

Ser  Thr  Gly  Gly  Gly  Glu  Val  Val  Arg  Tyr  Met  Ala  Arg  His  Pro  Ala
               100                 105                       110

Asp  Lys  Val  Ala  Lys  Ala  Val  Leu  Ile  Ala  Ala  Val  Pro  Pro  Leu  Met
          115                      120                 125

Val  Gln  Thr  Pro  Asp  Asn  Pro  Gly  Gly  Leu  Pro  Lys  Ser  Val  Phe  Asp
     130                 135                      140

Gly  Phe  Gln  Ala  Gln  Val  Ala  Ser  Asn  Arg  Ala  Gln  Phe  Tyr  Arg  Asp
145                 150                      155                      160

Val  Pro  Ala  Gly  Pro  Phe  Tyr  Gly  Tyr  Asn  Arg  Pro  Gly  Val  Asp  Ala
               165                      170                      175

Ser  Glu  Gly  Ile  Ile  Gly  Asn  Trp  Trp  Arg  Gln  Gly  Met  Ile  Gly  Ser
               180                      185                      190

Ala  Lys  Ala  His  Tyr  Asp  Gly  Ile  Val  Ala  Phe  Ser  Gln  Thr  Asp  Phe
          195                 200                      205

Thr  Glu  Asp  Leu  Lys  Gly  Ile  Thr  Gln  Pro  Val  Leu  Val  Met  His  Gly
     210                      215                      220

Asp  Asp  Asp  Gln  Ile  Val  Pro  Tyr  Glu  Asn  Ser  Gly  Leu  Leu  Ser  Ala
225                 230                      235                      240

Lys  Leu  Leu  Pro  Asn  Gly  Thr  Leu  Lys  Thr  Tyr  Gln  Gly  Tyr  Pro  His
               245                      250                      255

Gly  Met  Pro  Thr  Thr  His  Ala  Asp  Val  Ile  Asn  Ala  Asp  Leu  Leu  Ala
               260                      265                      270

Phe  Ile  Arg  Ser
               275
```

( 2 ) INFORMATION FOR SEQ ID NO:3:

( i ) SEQUENCE CHARACTERISTICS:
        ( A ) LENGTH: 1120 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pseudomonas putida
        ( B ) STRAIN: MR-2068 (FERM BP- 3846)

( i x ) FEATURE:
        ( A ) NAME/KEY: 93-923 CDS ( x i ) SEQUENCE DESCRIPTION: SEQ ID NO:3:

```
CTGCAGTGCA  GTCACCACAA  ATTCCGGCGC  CAAGCAAAAT  TCCTCCTATT  CTCAATAGCT      60
CACTTCGCTT  CCTGCACACA  GGAGACCCGA  CCATGAGCTA  TGTAACCACG  AAGGACGGCG     120
```

```
TACAGATCTT  CTACAAGGAC  TGGGGCCCGC  GCGATGCGCC  GGTCATCCAC  TTCCACCACG        180

GCTGGCCGCT  CAGTGCCGAC  GACTGGGACG  CGCAGATGCT  GTTCTTCCTC  GCCCACGGTT        240

ACCGCGTGGT  CGCCCACGAC  CGCCGCGGCC  ATGGCCGCTC  CAGCCAGGTA  TGGGACGGCC        300

ACGACATGGA  CCACTACGCC  GACGACGTAG  CCGCAGTGGT  GGCCCACCTG  GCATTCAGG         360

GCGCCGTGCA  TGTCGGCCAC  TCGACCGGTG  GCGGTGAGGT  GGTGCGCTAC  ATGGCCCGAC        420

ACCCTGCAGA  CAAGGTGGCC  AAGGCCGTGC  TGATCGCCGC  CGTACCGCCG  TTGATGGTGC        480

AGACTCCCGA  TAATCCCGGT  GGCCTGCCCA  AATCCGTTTT  CGACGGCTTC  CAGGCCCAGG        540

TCGCCAGCAA  CCGCGCGCAG  TTCTACCGGG  ATGTGCCGGC  AGGGCCGTTC  TACGGCTACA        600

ACCGCCCCGG  TGTCGACGCC  AGCGAAGGCA  TCATCGGCAA  CTGGTGGCGC  CAGGGCATGA        660

TCGGTAGCGC  CAAGGCCCAT  TACGATGGCA  TCGTGGCGTT  TTCCAGACC   GACTTCACCG        720

AAGACCTGAA  GGGCATTACC  CAGCCGGTGC  TGGTGATGCA  TGGCGACGAC  GACCAGATCG        780

TGCCGTATGA  GAACTCCGGG  CTGCTGTCGG  CCAAGCTGCT  GCCCAATGGC  ACACTGAAGA        840

CCTACCAGGG  CTACCCGCAT  GGCATGCCGA  CCACCCATGC  CGATGTGATC  AATGCGGATT        900

TGCTGGCGTT  TATCCGTAGC  TGATGTGATC  GCCTGCACCG  GCCTCTTCGC  GGGCACTGGC        960

AACACACCTC  CCCCAGGATT  ACCATGTCAC  GCTTCTAGTG  CGGCCCTTTG  CCGCCCCTTG       1020

CCTCCCTGCC  TGCCAAAACC  CCATGCCCTT  CGAACTCACC  GTAGAACCCC  TCACCCTGCT       1080

GATCCTGGCC  CTGGTCGCCT  TCGTCGCCGG  TTTCATCGAT                              1120
```

( 2 ) INFORMATION FOR SEQ ID NO:4:

( i ) SEQUENCE CHARACTERISTICS:
        ( A ) LENGTH: 1329 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pseudomonas putida
        ( B ) STRAIN: MR-2068 (FERM- 3846)

( i x ) FEATURE:
        ( A ) NAME/KEY: mat-peptide
        ( B ) LOCATION: 302..1129
        ( C ) IDENTIFICATION METHOD: dideoxy chain termination
            method (F. Sanger)

( x i ) SEQUENCE DESCRIPTION: SEQ ID NO:4:

```
CCCGGGCCGT  GAGCGATGCC  ATCCTCGGTG  ACGACGACCT  GCTGGCGCTA  TATCAAGGCA         60

TCGACAACGG  CCGCTTCCCC  GGTGGCGACC  TGCTGGCCGC  ACCGCTGGAA  GCCGCCGCCA        120

AGGCCTGGTA  CCGGATGCGC  GACCGCGCCT  GATCGCCTGG  CACCGCTCCT  ACACGGCGCC        180

GGGCAGGCCG  GAAGCATGGT  GCAAGCCCAC  TGCAGTGCAG  TCACCACAAA  TTCCGGCGCC        240

AAGCAAAATT  CCTCCTATTC  TCAATAGCTC  ACTTCGCTTC  CTGCACACAG  GAGACCCGAC        300
```

```
C  ATG  AGC  TAT  GTA  ACC  ACG  AAG  GAC  GGC  GTA  CAG  ATC  TTC  TAC  AAG        346
   Met  Ser  Tyr  Val  Thr  Thr  Lys  Asp  Gly  Val  Gln  Ile  Phe  Tyr  Lys
    1              5                    10                       15

GAC  TGG  GGC  CCG  CGC  GAT  GCG  CCG  GTC  ATC  CAC  TTC  CAC  CAC  GGC  TGG        394
Asp  Trp  Gly  Pro  Arg  Asp  Ala  Pro  Val  Ile  His  Phe  His  His  Gly  Trp
              20                       25                       30

CCG  CTC  AGT  GCC  GAC  GAC  TGG  GAC  GCG  CAG  ATG  CTG  TTC  TTC  CTC  GCC        442
Pro  Leu  Ser  Ala  Asp  Asp  Trp  Asp  Ala  Gln  Met  Leu  Phe  Phe  Leu  Ala
         35                       40                       45
```

| | | | | | | | | | | | | | | | | |
|---|---|---|---|---|---|---|---|---|---|---|---|---|---|---|---|---|
| CAC | GGT | TAC | CGC | GTG | GTC | GCC | CAC | GAC | CGC | CGC | GGC | CAT | GGC | CGC | TCC | 490 |
| His | Gly | Tyr 50 | Arg | Val | Val | Ala | His 55 | Asp | Arg | Arg | Gly | His 60 | Gly | Arg | Ser | |
| AGC | CAG | GTA | TGG | GAC | GGC | CAC | GAC | ATG | GAC | CAC | TAC | GCC | GAC | GAC | GTA | 538 |
| Ser | Gln 65 | Val | Trp | Asp | Gly | His 70 | Asp | Met | Asp | His | Tyr 75 | Ala | Asp | Asp | Val | |
| GCC | GCA | GTG | GTG | GCC | CAC | CTG | GGC | ATT | CAG | GGC | GCC | GTG | CAT | GTC | GGC | 586 |
| Ala 80 | Ala | Val | Val | Ala | His 85 | Leu | Gly | Ile | Gln | Gly 90 | Ala | Val | His | Val | Gly 95 | |
| CAC | TCG | ACC | GGT | GGC | GGT | GAG | GTG | GTG | CGC | TAC | ATG | GCC | CGA | CAC | CCT | 634 |
| His | Ser | Thr | Gly | Gly 100 | Gly | Glu | Val | Val | Arg 105 | Tyr | Met | Ala | Arg | His 110 | Pro | |
| GCA | GAC | AAG | GTG | GCC | AAG | GCC | GTG | CTG | ATC | GCC | GCC | GTA | CCG | CCG | TTG | 682 |
| Ala | Asp | Lys 115 | Val | Ala | Lys | Ala | Val | Leu 120 | Ile | Ala | Ala | Val | Pro 125 | Pro | Leu | |
| ATG | GTG | CAG | ACT | CCC | GAT | AAT | CCC | GGT | GGC | CTG | CCC | AAA | TCC | GTT | TTC | 730 |
| Met | Val | Gln | Thr 130 | Pro | Asp | Asn | Pro | Gly 135 | Gly | Leu | Pro | Lys 140 | Ser | Val | Phe | |
| GAC | GGC | TTC | CAG | GCC | CAG | GTC | GCC | AGC | AAC | CGC | GCG | CAG | TTC | TAC | CGG | 778 |
| Asp | Gly | Phe 145 | Gln | Ala | Gln | Val | Ala 150 | Ser | Asn | Arg | Ala | Gln 155 | Phe | Tyr | Arg | |
| GAT | GTG | CCG | GCA | GGG | CCG | TTC | TAC | GGC | TAC | AAC | CGC | CCC | GGT | GTC | GAC | 826 |
| Asp 160 | Val | Pro | Ala | Gly | Pro 165 | Phe | Tyr | Gly | Tyr | Asn 170 | Arg | Pro | Gly | Val | Asp 175 | |
| GCC | AGC | GAA | GGC | ATC | ATC | GGC | AAC | TGG | TGG | CGC | CAG | GGC | ATG | ATC | GGT | 874 |
| Ala | Ser | Glu | Gly | Ile 180 | Ile | Gly | Asn | Trp | Trp 185 | Arg | Gln | Gly | Met | Ile 190 | Gly | |
| AGC | GCC | AAG | GCC | CAT | TAC | GAT | GGC | ATC | GTG | GCG | TTT | TCC | CAG | ACC | GAC | 922 |
| Ser | Ala | Lys | Ala | His 195 | Tyr | Asp | Gly | Ile | Val 200 | Ala | Phe | Ser | Gln | Thr 205 | Asp | |
| TTC | ACC | GAA | GAC | CTG | AAG | GGC | ATT | ACC | CAG | CCG | GTG | CTG | GTG | ATG | CAT | 970 |
| Phe | Thr | Glu 210 | Asp | Leu | Lys | Gly | Ile 215 | Thr | Gln | Pro | Val | Leu 220 | Val | Met | His | |
| GGC | GAC | GAC | GAC | CAG | ATC | GTG | CCG | TAT | GAG | AAC | TCC | GGG | CTG | CTG | TCG | 1018 |
| Gly | Asp | Asp 225 | Asp | Gln | Ile | Val | Pro 230 | Tyr | Glu | Asn | Ser 235 | Gly | Leu | Leu | Ser | |
| GCC | AAG | CTG | CTG | CCC | AAT | GGC | ACA | CTG | AAG | ACC | TAC | CAG | GGC | TAC | CCG | 1066 |
| Ala Lys 240 | Leu | Leu | Pro | Asn | Gly 245 | Thr | Leu | Lys | Thr | Tyr 250 | Gln | Gly | Tyr | Pro 255 | | |
| CAT | GGC | ATG | CCG | ACC | ACC | CAT | GCC | GAT | GTG | ATC | AAT | GCG | GAT | TTG | CTG | 1114 |
| His | Gly | Met | Pro | Thr 260 | Thr | His | Ala | Asp | Val 265 | Ile | Asn | Ala | Asp | Leu 270 | Leu | |
| GCG | TTT | ATC | CGT | AGC | TGATGTGATC | GCCTGCACCG | GCCTCTTCGC | GGGCACTGGC | | | | | | | | 1169 |
| Ala | Phe | Ile | Arg 275 | Ser | | | | | | | | | | | | |
| AACACACCTC | CCCCAGGATT | ACCATGTCAC | GCTTCTAGTG | CGGCCCTTTG | CCGCCCCTTG | | | | | | | | | | | 1229 |
| CCTCCCTGCC | TGCCAAAACC | CCATGCCCTT | CGAACTCACC | GTAGAACCCC | TCACCCTGCT | | | | | | | | | | | 1289 |
| GATCCTGGCC | CTGGTCGCCT | TCGTCGCCGG | TTTCATCGAT | | | | | | | | | | | | | 1329 |